(12) United States Patent
Schuijers

(10) Patent No.: US 10,722,183 B2
(45) Date of Patent: Jul. 28, 2020

(54) SLEEP SIGNAL CONDITIONING DEVICE AND METHOD

(71) Applicant: KONINKLIJKE PHILIPS N.V., Eindhoven (NL)

(72) Inventor: Erik Gosuinus Petrus Schuijers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 69 days.

(21) Appl. No.: 16/092,578

(22) PCT Filed: Apr. 6, 2017

(86) PCT No.: PCT/EP2017/058171
§ 371 (c)(1),
(2) Date: Oct. 10, 2018

(87) PCT Pub. No.: WO2017/178308
PCT Pub. Date: Oct. 19, 2017

(65) Prior Publication Data
US 2019/0167207 A1    Jun. 6, 2019

(30) Foreign Application Priority Data

Apr. 15, 2016  (EP) .................................... 16165483

(51) Int. Cl.
*A61B 5/00*   (2006.01)
*A61B 5/0205* (2006.01)
(Continued)

(52) U.S. Cl.
CPC ............ *A61B 5/7278* (2013.01); *A61B 5/024* (2013.01); *A61B 5/0205* (2013.01);
(Continued)

(58) Field of Classification Search
CPC ..... A61B 5/0205; A61B 5/024; A61B 5/0816; A61B 5/11; A61B 5/1102; A61B 5/1118;
(Continued)

(56) References Cited

U.S. PATENT DOCUMENTS 4,686,999 A * 8/1987 Snyder ................. A61B 5/0816
600/529
6,280,392 B1 8/2001 Yoshimi
(Continued)

FOREIGN PATENT DOCUMENTS

| WO | 2013179189 A1 | 12/2013 |
|---|---|---|
| WO | 2015078937 A1 | 6/2015 |
| WO | 2015078940 A1 | 6/2015 |

*Primary Examiner* — Carl H Layno
*Assistant Examiner* — Jane C Kalinock (57) ABSTRACT

A method and device are provided for conditioning a sleep signal from a sleep sensor for a sleep monitor. A sleep sensor is configured to sense a physiological signal, such as a cardiac or respiratory signal from a sleeping mammal, such as a human, e.g. an infant or a baby. If the mammal exhibits also (gross) body movement during his sleep, the sensor signal may be clipped. The method and device provide a conditioning of the sleep signal by providing an estimation of the sleep signal instead of the conditioned sleep signal itself when the sensor signal is clipping.

15 Claims, 5 Drawing Sheets

(51) Int. Cl.
*A61B 5/024* (2006.01)
*A61B 5/08* (2006.01)
*A61B 5/11* (2006.01)

(52) U.S. Cl.
CPC .............. *A61B 5/0816* (2013.01); *A61B 5/11* (2013.01); *A61B 5/1102* (2013.01); *A61B 5/1118* (2013.01); *A61B 5/4809* (2013.01); *A61B 5/6892* (2013.01); *A61B 5/7221* (2013.01); *A61B 2562/0247* (2013.01)

(58) Field of Classification Search
CPC ... A61B 5/4809; A61B 5/6892; A61B 5/7221; A61B 5/7278; A61B 2562/0247
USPC ......................................................... 600/301
See application file for complete search history.

(56) References Cited

U.S. PATENT DOCUMENTS

| | | |
|---|---|---|
| 7,643,921 B2 | 1/2010 | Andres |
| 2009/0093687 A1 | 4/2009 | Telfort |
| 2010/0231794 A1* | 9/2010 | Robertson ............. H03M 1/185 |
| | | 348/572 |
| 2011/0087113 A1 | 4/2011 | Mack |
| 2015/0216475 A1 | 8/2015 | Luna |
| 2016/0007870 A1* | 1/2016 | Brueser ................ A61B 5/6892 |
| | | 600/509 |

* cited by examiner

FIG. 5

SLEEP SIGNAL CONDITIONING DEVICE AND METHOD

This application is the U.S. National Phase application under 35 U.S.C. § 371 of International Application No. PCT/EP2017/058171 filed on Apr. 6, 2017, which claims the benefit of International Application No. 16165483.5 filed on Apr. 15, 2016. These applications are hereby incorporated by reference herein.

FIELD OF THE INVENTION

The invention relates to a sleep signal conditioning device, method and system for a sleep monitor. The invention further relates to a computer program product comprising instructions for causing a processor system to perform the method.

A sleep monitor may be used to detect the sleep of a mammal, such as a human, for example an infant or a baby. Especially for infants, parents or medical personnel may want to monitor the sleep process. During sleep the mammal may exhibit (gross) body movement as well as emanate physiological signals, such as cardiac or respiratory signals that may be picked up by sensors of a sleep monitor. A sensor for monitoring body movement is typically configured for sensing relatively large amplitude signals compared to sensors for monitoring a physiological signal.

A sensor able to sense both body movement and physiological signals with an adequate accuracy requires a large dynamic range. Dynamic range, abbreviated DR or DNR, is defined as the ratio between the largest and smallest values of a changeable quantity.

BACKGROUND OF THE INVENTION

It is known that piezoelectric sensors positioned under a mattress are suitable for extracting physiological signals, such as cardiac or respiratory signals during little to no motion, and are also suitable for extracting (gross) body movement when the person lying on top of the mattress is moving.

However, in practice it turns out that a huge dynamic range is required to capture both the physiological signals during little to no motion, which are extremely low amplitude signals and the movement signals during motion, which are extremely large amplitude signals. Therefore sleep signal conditioning devices are typically configured to condition the sensor signals to enable measuring the physiological signals in the presence of large signals.

WO2015/078940 proposes to apply an adjustable attenuation to the sensor signal, such that small and large amplitude sensor signals are measurable. The magnitude attenuation factor is taken into account when determining the biophysical variable.

WO 2013/179189 A1 discloses a cardiac activity and respiratory activity, which are monitored of a person lying on a surface of a supporting system. A first signal is generated by sampling a magnitude of a first physical quantity that is representative of the ballistic effect of cardiac activity in the horizontal direction. A second signal is generated by sampling the magnitude of a second physical quantity. The second physical quantity is representative of a change in a pushing effect of the body on the surface in a vertical direction. The changing pushing effect is due to a combination of the expanding and contracting of the body as a result of respiratory activity and of the ballistic effect of cardiac activity in the vertical direction. The first signal and the second signal are processed to extract information about the ballistic effect of the cardiac activity in both the horizontal direction and the vertical direction, and a fourth signal representative of respiratory activity. The first signal is used for identifying in the second signal a contribution from the ballistic effect of cardiac activity in the vertical direction.

US 2009/0093687 A1 discloses a method of communicating with a physiological sensor. In an embodiment, the method includes supplying power through a first conductor in a first mode to the physiological sensor and communicating with an information element through the first conductor in a second mode. The physiological sensor includes the information element, a power supply configured to receive and store power from the first conductor in the first mode, and sensing circuitry configured to receive power from the first conductor in the first mode. The power supply releases the stored power to the sensing circuitry in the second mode.

US 2016/0007870 A1 provides a method of processing a signal representing a physiological rhythm of a subject, wherein the method comprises the steps of receiving the signal from the subject, filtering the signal with a band pass filter, extracting an analysis window from the filtered signal, performing a plurality of interval length estimation methods on the filtered signal in the analysis window, summing the outputs of the plurality of interval length estimation methods, and determining an interval length from the sum of the outputs of the plurality of interval length estimation methods.

WO 2015/078937 A1 discloses a sleep monitoring device for monitoring sleep states of a human, the sleep monitoring device is configured to receive movement data of the resting human from a movement measurement device, the sleep monitoring device comprises a movement data analyzer configured to compute from the movement data at least: heart beat data and respiration data, and physical activity, a data classifier configure to determine a heart rate regularity valuation of the heart beat data within a time interval, and to determine a respiration regularity valuation of the respiration data within the time interval, a sleep classifier configured to obtain a sleep state for the time interval from at least the respiration regularity valuation and the heart rate regularity valuation.

US 2015/0216475 A1 discloses electrodes and methods to determine physiological states using a wearable device (or carried device) and one or more sensors that can be subject to motion. A method includes receiving a sensor signal including data representing physiological characteristics in a wearable device from a distal end of a limb and a motion sensor signal. The method includes decomposing at a processor the sensor signal to determine physiological signal components. A physiological characteristic signal is generated that includes data representing a physiological characteristic, which can form a basis to determine a physiological state based on, for example, bioimpedance signals originating from the distal end of the limb.

SUMMARY OF THE INVENTION

It would be advantageous to have a device, a method or a system for conditioning the measured sensor signals to mitigate the drawback of having an adjustable attenuation circuit.

According to an aspect of the invention a sleep signal conditioning device for a sleep monitor comprises a first processing unit for providing a first parameter indicative of the magnitude of a first sensor signal from a first sleep sensor sensing a physiological signal from a sleeping mammal; a second processing unit for providing a second parameter indicative of the magnitude of a second sensor signal from a second sleep sensor sensing a physiological signal from the sleeping mammal, wherein the first sensor signal is different from the second sensor signal; a clipping detector for detecting when the first sensor signal is clipping; a divider for calculating a ratio based on dividing the first parameter by the second parameter when the first sensor signal is not clipping; a multiplier for generating an estimated first sensor signal) based on multiplying a second output signal based on the second sensor signal by the ratio; and a switch for providing a first output sleep signal based on the estimated first sensor signal when detecting that the first sensor signal is clipping and a first output signal based on the first sensor signal when detecting that the first sensor signal is not clipping.

According to another aspect of the invention, a sleep signal conditioning method for a sleep monitor comprises the steps of processing a first sensor signal for providing a first parameter indicative of the magnitude of the first sensor signal from a first sleep sensor sensing a physiological signal from a sleeping mammal; processing a second sensor signal for providing a second parameter indicative of the magnitude of the second sensor signal from a second sleep sensor sensing a physiological signal from the sleeping mammal, wherein the first sensor signal is different from the second sensor signal; detecting when the first sensor signal is clipping; calculating a ratio based on dividing the first parameter by the second parameter when the first sensor signal is not clipping; generating an estimated first sensor signal based on multiplying a second output signal based on the second sensor signal by the ratio; and providing a first output sleep signal based on the estimated first sensor signal when detecting that the first sensor signal is clipping and a first output signal based on the first sensor signal when detecting that the first sensor signal is not clipping.

The invention mitigates the above drawback in a multi-sensor configuration by determining a first estimated signal to replace a first clipped signal based on a second sensor signal from a different sensor and a ratio of the first sensor signal to the second sensor signal. During motion the energy of clipped signal portions is estimated from non-clipped signal portions of different sensor signals and a relative energy profile called ratio that is constructed in the background. The ratio between the first and second sensor signal is established by said divider in a time period that the first sensor signal is not clipping. The divider receives respective parameters indicative of the magnitude of the respective signals, so not the signal itself but rather a parameter related to the magnitude of the signal, e.g. the amplitude of the signal, the envelope of the signal or the power of the signal. Such parameters of respective different sensor signals are divided to determine the ratio in a period when the signals are not clipping. The multiplier multiplies the second sensor signal by the ratio to provide an estimate of the first sensor signal, which estimate is switched to the sleep signal output during clipping of the first sensor signal. The first and second sensor signal may be conditioned versions of the corresponding sensor signals, while the conditioning may be shared with said processing for determining the respective parameters. Hence the invention provides a solution using multiple sensors in sleep monitoring system with a limited dynamic range in an environment with large differences in amplitude of the monitored signals.

The inventors considered extending the dynamic range by using a sensor with a logarithmic scale. Logarithmic sensors are able to measure high amplitude and low amplitude providing a high dynamic range. A disadvantage of these logarithmic sensors is that they are typically more complex. Therefore, a linear sensor in combination with a sleep signal conditioning device that copes with the large dynamic range is proposed. The conditioning device provides an output sleep signal proportional to the linear sensor signal by using the estimated ratio when sensor signals are clipping. The proposed signal conditioning device advantageously provides an accurate signal of physiological signals during sleep, while also providing a proportionally correct signal during gross body movement. So the conditioning device in effect restores or approximates the original dynamic range by using the estimated signal during clipping.

In an embodiment, the parameter indicative of the magnitude of the signal may be an amplitude estimation or an energy estimation of the signal. The energy of a signal is typically represented by the square of the signal. Another example of processing to derive the parameter indicative of the magnitude may be to take a peak-to-peak value, the average amplitude or the absolute value of the signal. The absolute value of the signal provides the advantage that typically in sleep monitoring the intensity is of interest and not the sign of the signal.

The processing of the signal may involve processing of multiple values of the signal in a filter, such as with a FIR or IIR filter. Such a filter provides a more stable processed signal over a time period.

Optionally in the device at least one of the processing units is arranged to determine the parameter indicative of the magnitude of the signal based also on a signal portion after a preceding signal portion where the first sensor signal was clipping, while the divider is arranged to use the determined parameter in the calculation of the ratio used during said preceding signal portion. Such conditioning device may be considered a non-real-time conditioning device. The device provides a ratio based on not only previous or current samples of a first and second sensor signal, but also on subsequent samples of the first and second sensor signal after a period of clipping. For example, such a non-real time device may introduce a large latency, e.g. recording a whole night of data, and only after having received the whole night of data, the above processing is started on the stored data.

Optionally in the device an ability to extract respiratory and cardiac features from a current signal portion is determined and the divider is arranged in dependence thereon to control whether or not to include the current signal portion in the calculation of the ratio. Alternatively, or additionally to filtering the energy values over time before updating the energy ratios to obtain a stable relative energy ratio matrix, the ability to extract respiratory and cardiac features may be employed to determine whether or not to include the current signal portion in the determination of the relative energy ratio mix. This means that only when the signal contained respiratory and cardiac information, and by that it is a stable signal, it is included.

Optionally, the device comprises a first conditioning unit for conditioning the first sensor signal to the first output signal and a second conditioning unit for conditioning the second sensor signal to the second output signal.

Optionally the first parameter as provided by the first processing circuit constitutes the first output signal and the second parameter as provided by the second processing circuit constitutes the second output signal.

Optionally in the device the first and/or second processing units are arranged to prohibit that respectively the first and/or second sensor signals influence the ratio when at least one of the first and second sensor signals are clipping.

Optionally the device comprises a plurality of processing units for processing a plurality of sensor signals from a respective plurality of sleep sensors; a plurality of clipping detectors for detecting when a respective one of the sensor signals is clipping; at least one divider for calculating a ratio matrix, wherein each element of the ratio matrix is a ratio based on dividing, when the respective sensor signals are not clipping, respective parameters indicative of the amplitude of respective sensor signals; at least one multiplier for generating at least one respective estimated signal based on multiplying a selected output signal based on a selected other one of the sensor signals by the respective element of the ratio matrix; and a plurality of switches for providing per switch a respective sleep output signal based on the respective estimated signal when detecting that the respective signal is clipping and based on a respective output signal based on the respective signal when detecting that the respective signal is not clipping. Advantageously, when a specific sensor signal is clipping, from the plurality of sensor signals one other sensor signal is selected from the plurality so as to provide the respective estimated output signal by multiplying that selected output signal by a corresponding element from the ratio matrix defining the ratio between the output signal of the clipping sensor and the selected other sensor. The selection may be based on determining which sensors are clipping, and/or which sensors have the closest relation to the clipping sensor, e.g. based on position of the sensors or signal quality.

According to another aspect of the invention, a computer program or a computer readable medium may have computer readable code embodied therein, the computer readable code being such that, on execution by a suitable computer or processor, the computer or processor is caused to perform the method as mentioned previously.

Modifications and variations of the system and/or the computer program product, which correspond to the described modifications and variations of the method, can be carried out by a person skilled in the art on the basis of the present description.

BRIEF DESCRIPTION OF THE DRAWINGS

These and other aspects of the invention are apparent from and will be elucidated with reference to the embodiments described hereinafter. In the drawings, FIG. 1 schematically shows a sleep monitoring system comprising a first sensor, a second sensor and a sleep signal conditioning device.

It is noted that the figures are purely diagrammatic and not drawn to scale. In the figures, elements which correspond to elements already described may have the same reference numerals.

DETAILED DESCRIPTION OF THE EMBODIMENTS

Ballistocardiography may be based on piezo-electric sensors. One or more piezo-electric sensors are put in a module that is placed under the mattress. A piezo-electric sensor will produce a small voltage when pressure is applied on it. Therefore, by logging the voltage of the sensor, movements of the person lying on top of the mattress are being captured. As it turns out, these sensors can be sufficiently sensitive to even capture respiratory and cardiac signals when the person lying on top of the mattress is lying still. So parameters are captured related to sleep: (gross body) movement, cardiac features (e.g. heart rate) and respiratory features (e.g. respiration rate).

Figure 5:
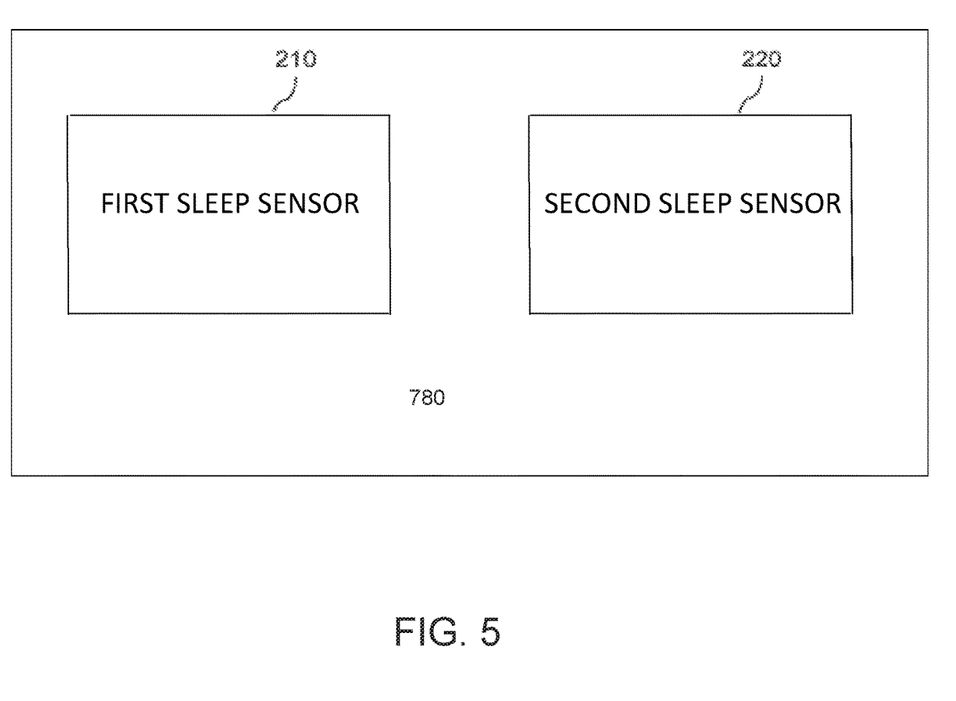
FIG. 5 illustrates an embodiment of a mattress including first and second sleep sensors.

Applying multiple sensors allows estimating the position and/or orientation of the baby/person. For sleep monitoring sensors are usually positioned in, under, adjacent to or in proximity of a mattress (780). For example, the sensors may be positioned on a frame supporting the mattress or positioned adjacent or inside the mattress. The sensors should be positioned such that a pressure fluctuation propagates to the sensors. The sensors may be spaced some distance from each other. The sensors may also have a dynamic range and/or accuracy distinct, such as different, from each other.

A mammal, such as a person, may be using the mattress (780) for sleeping. During sleeping the subject will breathe, have a heart beat and may also move. A sensor for measuring this diverse range of properties needs to have a high dynamic range as well as a high accuracy. Without resorting to the use of very specialised and/or costly sensors and signal processing, the invention uses a sensor signal from one sensor to compensate for another sensor signal that is clipping, as described below.

Sleep sensors are for sensing (gross) body movement and one or more physiological signals, such as a cardiac or respiratory signal. A sleep sensor may be a sensor comprising a pressure plate. A sleep sensor may be a piezoelectric sensor, such as a piezoelectric pressure sensor or piezoelectric strain sensor. In an embodiment a single sensor device comprises multiple piezo sensors, e.g. an arrangement of four sensors. The four sensors are arranged to the four corners of a square or rectangle.

Piezoelectric sensors suitable for extracting physiological signals, such as cardiac or respiratory signals during little to no motion, are also suitable for extracting (gross) body movement when the person lying on top of a mattress is moving. However, in practice it turns out that a huge dynamic range is required to capture both the physiological signals during little to no motion producing extremely low amplitude signals and the movement during motion producing extremely large amplitude signals. As a consequence, often the circuitry picking up the analogue voltage from the piezoelectric sensor(s) is configured in such a way that there is sufficient detail in the signals to capture the cardiac and respiratory features. Drawback of this is that the signals during motion are often clipped making it impossible to assess the level of motion. One can then only detect that there was motion, it is mostly impossible to assess the level or intensity of motion.

Figure 1:
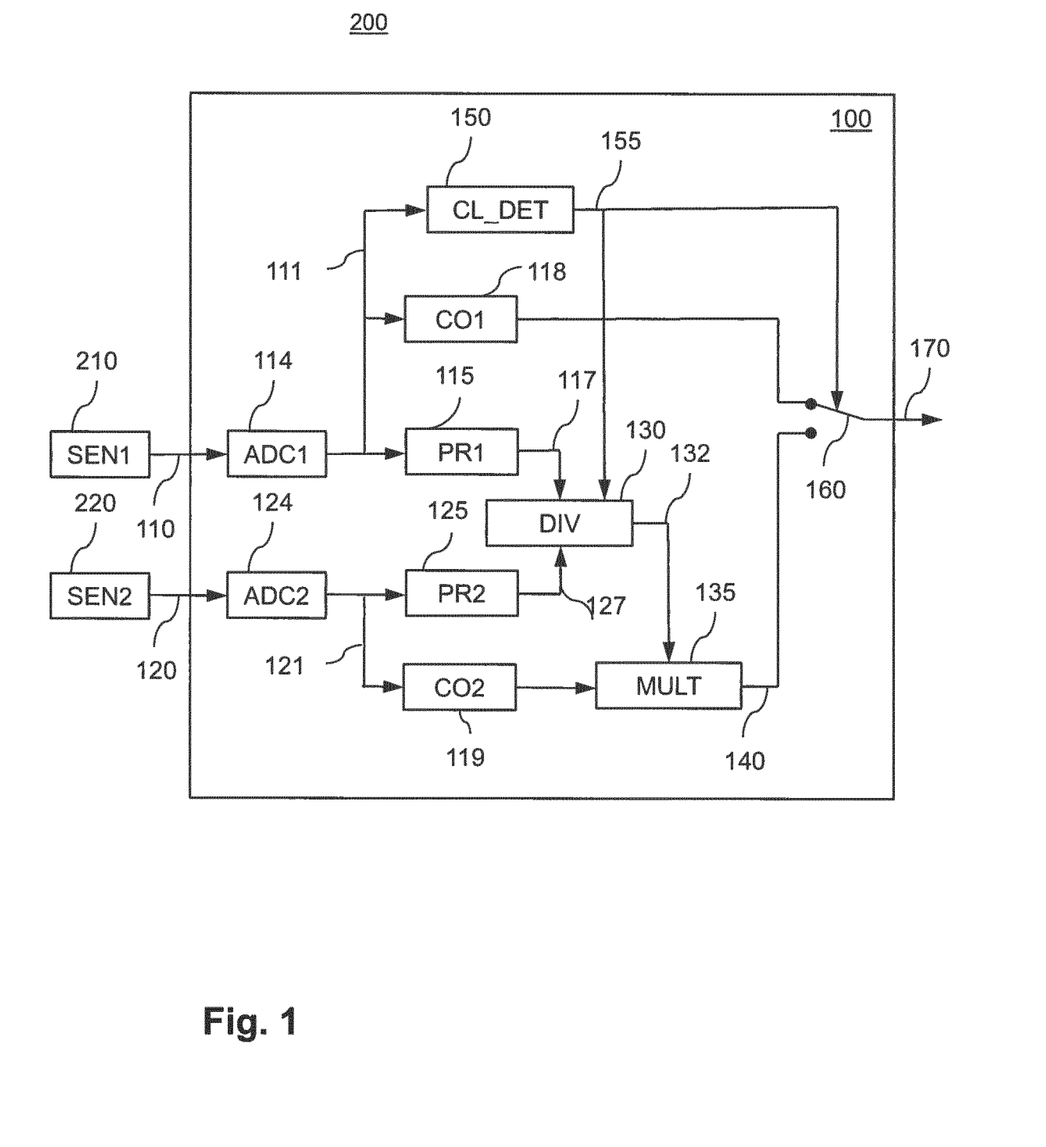

FIG. 1 schematically shows an example of a sleep monitoring system 200 comprising a first sensor 210, a second sensor 220 and a sleep signal conditioning device 100. The first and second sensors are coupled to respective inputs of the conditioning device for providing a first sensor signal 110 and a second sensor signal 120. After conditioning the first sensor signal the conditioning device provides a conditioned sleep output signal 170 based on conditioning the first sensor signal. The sleep output signal may be coupled to a sleep monitor. In the further text generating and using only a single signal is discussed. In practice (not shown), in addition to providing the first sleep signal output 170, typically similar sleep output signals would be generated based on the conditioned signals from the second and further sensors using corresponding processing circuitry.

The sleep monitoring system may further comprise a sleep monitor (not shown) for monitoring the sleep output signal 170 received from the conditioning device 100. The sleep monitor may be arranged to detect whether the mammal is actually sleeping or awake, and may further classify the sleep or sleep patterns over time. In a basic embodiment the output sleep signal 170 of FIG. 1 would be fed to a sleep/wake classifier, e.g. a Naïve Bayes classifier, to provide a prediction of whether the person/mammal is sleeping or not. Sleep detectors and classifiers are known as such, for example from patent documents U.S. Pat. No. 6,280,392 or WO2015/078940.

In a practical embodiment the sleep signal conditioning device 100 may be implemented in an integrated circuit or as a module on a printed circuit board carrying the conditioning circuit. Such conditioning circuit may be combined with the sleep monitor and/or the sensors to constitute a single device.

The conditioning circuit may comprise a first analogue-to-digital converter (ADC) 114 for providing a first digital sensor signal 111. The conditioning circuit may comprise a second ADC 124 for providing a second sensor signal 121. Typically, the first and second sensor signals are digitized and the digitized sensor signals are provided to the clipping detector and the first and second processing units. However processing of the analogue signals is also possible. The ADC may also be shared by multiplexing various signals, and may be preceded by an amplifier.

The sleep signal conditioning device may comprise a first sensor signal conditioning unit CO1 118 and a second sensor signal conditioning unit CO2 119 for conditioning the input sensor signal, for example buffering, scaling, noise filtering or frequency shaping such as band pass, high pass or low pass filtering. So the input sensor signals are conditioned to provide a conditioned sleep output signal. The conditioned first output signal may be analogue or digital. The conditioning may include scaling first output signal according to a logarithmic scale to provide a high accuracy of the first output signal at low amplitudes of a first sensor signal while still being able to provide signals representing high amplitude of the first sensor signal.

The conditioning may also include normalising the sleep output signal. Normalisation in the context of the invention means that the measured signals of different sensors are scaled to represent a same reference level. Normalisation may improve the performance of sleep detection and classification substantially. Normalisation in the context of the invention may involve positioning the measured signal in a range from 0 to 1 by scaling the complete signal to fit on this range. However, use of normalisation requires signals without clipping, because clipping would disturb the normalisation. Normalisation is typically done over a certain time period. This time period may vary from several minutes, an hour, several hours, a sleep cycle or even several sleep cycles. Such signals where clipping is corrected are provided by the conditioning device.

The conditioning circuit 100 comprises a first processing unit PR1 115 for processing the first sensor signal 110 for providing a first parameter 117, and a second processing unit PR2 125 for processing the second sensor signal 120 for providing a second parameter 127. The processing for determining the respective parameters may be (partly) shared with the above conditioning for determining the conditioned output signals. The processing units may have a finite impulse response (FIR) or infinite impulse response (IIR) filter. The processing units may be arranged to calculate the energy of the sensor signal, e.g. by a square operation. The processing unit may also comprise a combination of the above processing examples.

The device as shown in FIG. 1 has first and second conditioning units for conditioning the sensor signals to output signals and separate first and second processing units. Such processing may also be at least partly shared. For example, the first parameter as provided by the first processing circuit may constitute the first output signal and the second parameter as provided by the second processing circuit may constitute the second output signal.

The conditioning circuit further comprises a clipping detector 150 for detecting clipping of the first sensor signal 110. The clipping detector provides a clipping signal 155 indicating the clipping of the first sensor signal. Clipping may for example be detected if the signal from the ADC has a consecutive sequence of signal values at the maximum or minimum of the digital signal range of a predetermined length.

The conditioning circuit further comprises a divider 130 arranged to divide the first parameter 117 by the second parameter 127. The divider provides a ratio as output. So the ratio is calculated based on dividing the first parameter 117 derived from the first sensor signal and the corresponding parameter 127 derived from the second processed signal as provided by the respective processing units PR1 and PR2. In the example it is assumed that the first sensor signal is the larger signal and will start clipping, while the second sensor signal is not clipping. Similar processing may be applied to also provide an estimate of the second sensor signal when the second sensor signal is clipping based on a non-clipping first sensor signal, and equally so for further sensor signals.

The ratio is calculated by the divider based on unclipped first and second sensor signals, so in a period where both signal are relatively small. In an embodiment, when processing or conditioning of the signals involves multiple samples, such as in a FIR or IIR filter, information whether the first and/or second sensor signals are clipping may also be provided to the processing units PR1/2 and/or to the conditioning units CO1/2, which then may interrupt the processing to prevent clipped first and second sensor signals deteriorating their output signals. For example, clipped signal values may be omitted, filtering clock signals may be halted or a previous value may be replicated.

The conditioning circuit further comprises a multiplier MULT 135 for multiplying the ratio with the second processed sensor signal. The multiplier provides as output an estimated first sensor signal 140. The estimated signal is determined by multiplying the conditioned second sensor signal from CO2 by the ratio established by the divider.

In an embodiment the gain of the sensors is different, e.g. the gain of the first sensor signal in an amplifier in the ADC unit is higher or the sensitivity of the first sensor is higher than the second sensor. When determining the ratio, the gain difference is automatically taken into account by the divider because the processing units receive the differing signals when not clipping. When the ratio is above one due to a higher gain of the first sensor signal, the first sensor signal will usually start clipping first due to the higher gain. In a practical embodiment only high gain signals may be protected by the above signal replacement circuitry.

The conditioning circuit further comprises a switch 160. The switch is controlled by the clipping signal 155 of the clipping detector. The switch provides the conditioned sleep output signal 170 based on the estimated first sensor signal when detecting that the first sensor signal is clipping and a first output signal based on the first sensor signal when detecting that the first sensor signal is not clipping. In the case the first sensor signal is not clipping the conditioned first output is the first conditioned sensor signal from unit CO1. In the case the first sensor signal is clipping the conditioned first output is the estimated first sensor signal 140.

In an embodiment, during clipping of the first sensor signal processing of the first and/or second processing unit may be temporarily stopped, e.g. by maintaining the values present in the processing unit at their current values when the clipping signal indicates the start of clipping. Alternatively, during clipping of the first sensor signal the input of the first and/or second processing unit may be temporarily held at a stable or constant value. Alternatively, during clipping the ratio 132 may be kept stable or at a constant value. Alternatively, a combination of the above options is possible during clipping of the first sensor signal.

Although the signal processing as described in this document may be (partly) implemented by analogue units, a digital implementation is intended also. For example, the switch in a digital implementation may be an operation of overwriting a clipped signal by the estimated value (scaled by the ratio) of one of the other signals. The sleep signal conditioning device in the example may have a first processing unit and a second processing unit. However, the reader will understand that the processing may be done by a shared processing unit alternating between processing and/or conditioning the first sensor signal and the second sensor signal and further signals. Especially when the signals are digital, a shared signal processor may perform the above processing based on appropriate firmware. Such shared processing unit may also perform clipping detection, switching, multiplying and/or dividing.

The sensor signal is typically provided as digital sensor signal or is amplified and digitized by the conditioning device before being processed. Preferably clipping detection is applied on the digitized signals. If digitization is done by the conditioning device, the device may comprise one analogue-to-digital converter (ADC) with a multiplexer for providing the ADC with the different analogue signals, an ADC per digitized signal or a hybrid form. The sensor signals may be amplified before ADC processing. The gain factor of the amplifier may be predetermined or adjustable by the sleep signal conditioning device.

In an embodiment the sleep signal conditioning device may provide multiple conditioned output sleep signals and comprise a plurality of processing units for processing a plurality of signals from a respective plurality of sleep sensors. Multiple ratios may be calculated between some or all of the sensor signals. The calculation of the ratios may be performed consecutively by providing the respective parameters to at least one divider. The different ratios may be stored as elements of a ratio matrix. For detecting the clipping of multiple signals the conditioning device has one or more clipping detectors. One clipping detector receiving multiple signals may be employed for detecting clipping of multiple signals. Alternatively, each signal may have its own clipping detector.

The amount of switches or corresponding switching operations in a digital implementation in the device may be equal to the amount of conditioned output sleep signals, while each switch receives a respective estimated signal. Each estimated signal may be based on multiplying one of the other sensor signals with the respective ratio from the matrix. Multiple estimations of a single clipping signal may be calculated, e.g. by multiplying all other sensor signals with the appropriate ratio from the ratio matrix, and combined e.g. by an averaging. The averaging may be a weighted average, wherein the weight may depend on signal strength, clipping, stability and/or noise. In an alternative embodiment the device may provide multiple estimations to respective outputs. In an alternative embodiment the output signal may be interleaved or a multiplexed signal comprising at least two, preferably all, output signals.

Figure 2:
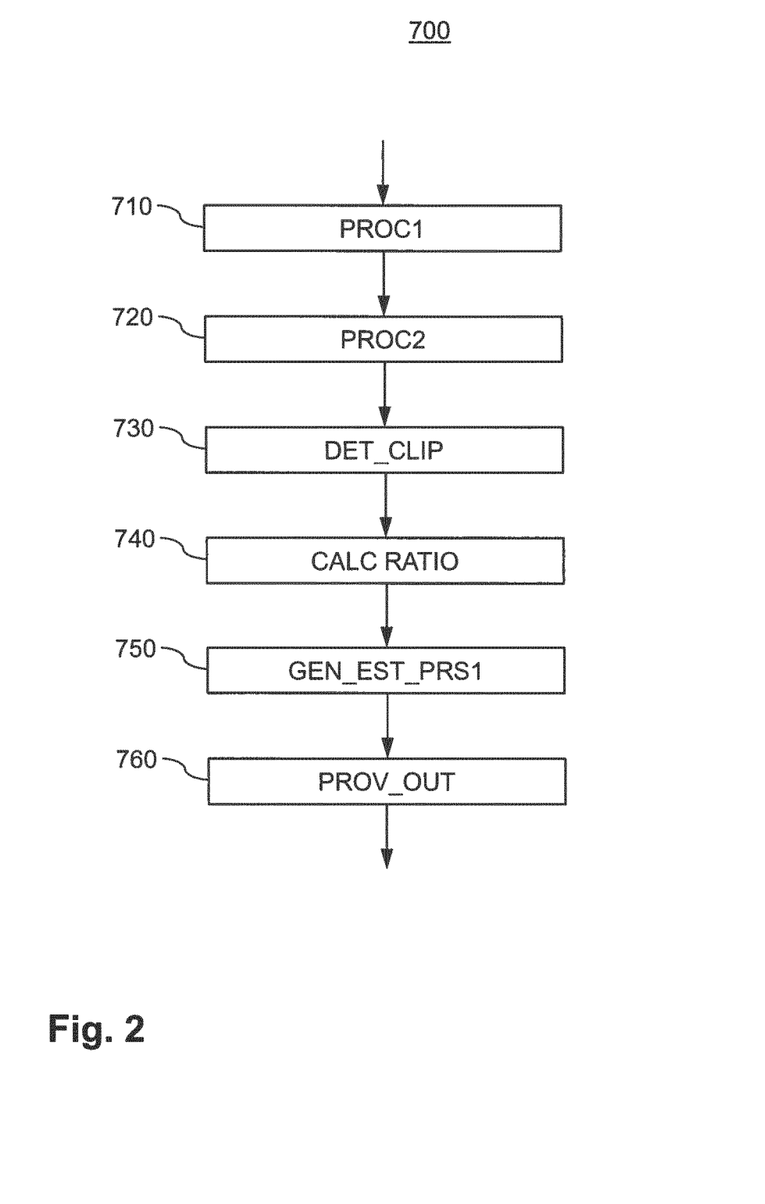
FIG. 2 schematically shows a sleep signal conditioning method for a sleep monitor.

FIG. 2 schematically shows a sleep signal conditioning method 700 for a sleep monitor. The method starts with processing PROC1 710 a first sensor signal to provide a first conditioned signal and a first parameter. The method continues with processing PROC2 720 a second sensor signal to provide a second parameter and a second conditioned signal. The steps of processing PROC1, PROC2 the first and second sensor signals may be swapped or done in parallel. The processing may involve FIR or IIR filtering of the respective signal, or other filtering or signal processing such as noise reduction, known as such in the field of signal conditioning.

There are two typical ways in which the energy levels can be determined: frame based or recursive. In a frame based solution, the signal is segmented into small portions of data, e.g. 5 seconds long. And the energy is calculated for each portion:

$$E_{k,c} = \sum_{n=0}^{h-1} x^2[n + k \cdot h]$$

where k denotes the frame index, c denotes the channel and h denotes the hop size.

In a recursive fashion the energy may be calculated as:

$$E[n]_c = \alpha E[n-1]_c + (1-\alpha)x^2[n]$$

Variations to both estimations can be realized, e.g. to eliminate DC signal before estimating the energy.

The method thereafter continues with DET_CLIP 730 for detecting if the first sensor signal is clipping. The detection of clipping of the first sensor signal in practice may be a continuous process in parallel with processing of the first sensor signal, the second sensor signal or further signals.

Clipping can be determined in a number of ways. Most straightforward is to use the calculated energy to basically find large signal spikes. Alternatively, a histogram could be constructed over a predefined window. If the histogram distribution has many values in the clipping area, it could be classified as a clipped region.

The method continues with calculating a ratio in step CALC RATIO 740. The ratio may be calculated based on dividing the first processed signal by the second processed signal. The calculation is to be done while the first sensor signal is not clipping as detected in the step DET_CLIP so that clipping of the first sensor signal has no influence on the ratio. This may require that the ratio is maintained or stored, or not updated, as long as the first sensor signal is clipping, because this prevents clipped signal values to influence the filtering.

In a matrix various relative energy ratios may be determined as follows. This can be visualized in the form of a triangular ratio matrix, in the example of four sensor channels:

|    | E1 | E2    | E3    | E4    |
|----|----|-------|-------|-------|
| E1 | —  | E2/E1 | E3/E1 | E4/E1 |
| E2 |    | —     | E3/E2 | E4/E2 |
| E3 |    |       | —     | E4/E3 |
| E4 |    |       |       | —     |

Since it is desirable to use a stable relative energy ratio to estimate energy during clipping it is recommended to low pass filter the energy ratios over time prior to calculating the energy ratios. It is noted that the recursive energy estimation easily allows such filtering by change of the parameter $\alpha$ in the above formula.

The method thereafter continues with step GEN_EST_PRS1 750 by generating an estimated first sensor signal. The estimated first sensor signal is based on the multiplication of the second conditioned signal with the ratio. Generating the estimated first sensor signal is performed when it is detected that the first sensor signal is clipping as detected in the step DET_CLIP.

The method thereafter continues with step PROV_OUT 760 by providing an output signal to a first sleep signal output. In the case the first sensor signal is not clipping the first conditioned signal is provided to the first sleep signal output. Otherwise the estimated first sensor signal is provided to the first output. Hereafter the method may repeat the above mentioned steps for continuously conditioning the first sensor signal.

In the above generating and outputting steps the determined ratios may be applied as follows. Assume that for our current frame k clipping is observed in channels 2, 3 and 4, whereas channel 1 is not considered as being clipped. In that case the old (clipped) energy estimate for channels 2, 3 and 4 is being overwritten by taking the energy of channel 1 and multiplying that by the (stable) ratios as determined above.

The methods generate and use only a single signal, but in practice, typically multiple signals would be generated for the second and further sensors using corresponding method steps.

The above presumes that the orientation of the person, and therefore the relative levels of energy are constant over time. Obviously, the relative levels may change as soon as a person has moved. So after a period of clipping the ratios may be recalculated using the parameters from after said period. Furthermore, if no real-time behaviour is required, a gain profile both before and after a clipping period may be used in establishing an energy ratio instead of just applying a ratio based on past data only.

There may be situations in which all four channels clip, due to extremely strong motion. If so detected, only a lower bound for the motion may be calculated using the signal with the smallest (stable) energy level as reference.

In an embodiment, alternatively to filtering the energy values over time before updating the energy ratios to obtain a stable relative energy ratio matrix, the ability to extract respiratory and cardiac features may be employed to determine whether or not to include the current signal portion in the determination of the relative energy ratio mix. This means that only when it is determined that a signal portion contained respiratory and cardiac information, and by that it is determined to be a stable and sufficiently reliable signal, the signal portion is included. Such determination may, for example, be performed in a detector circuit in the conditioning device or in a sleep monitor coupled to the conditioning device.

Figure 3:
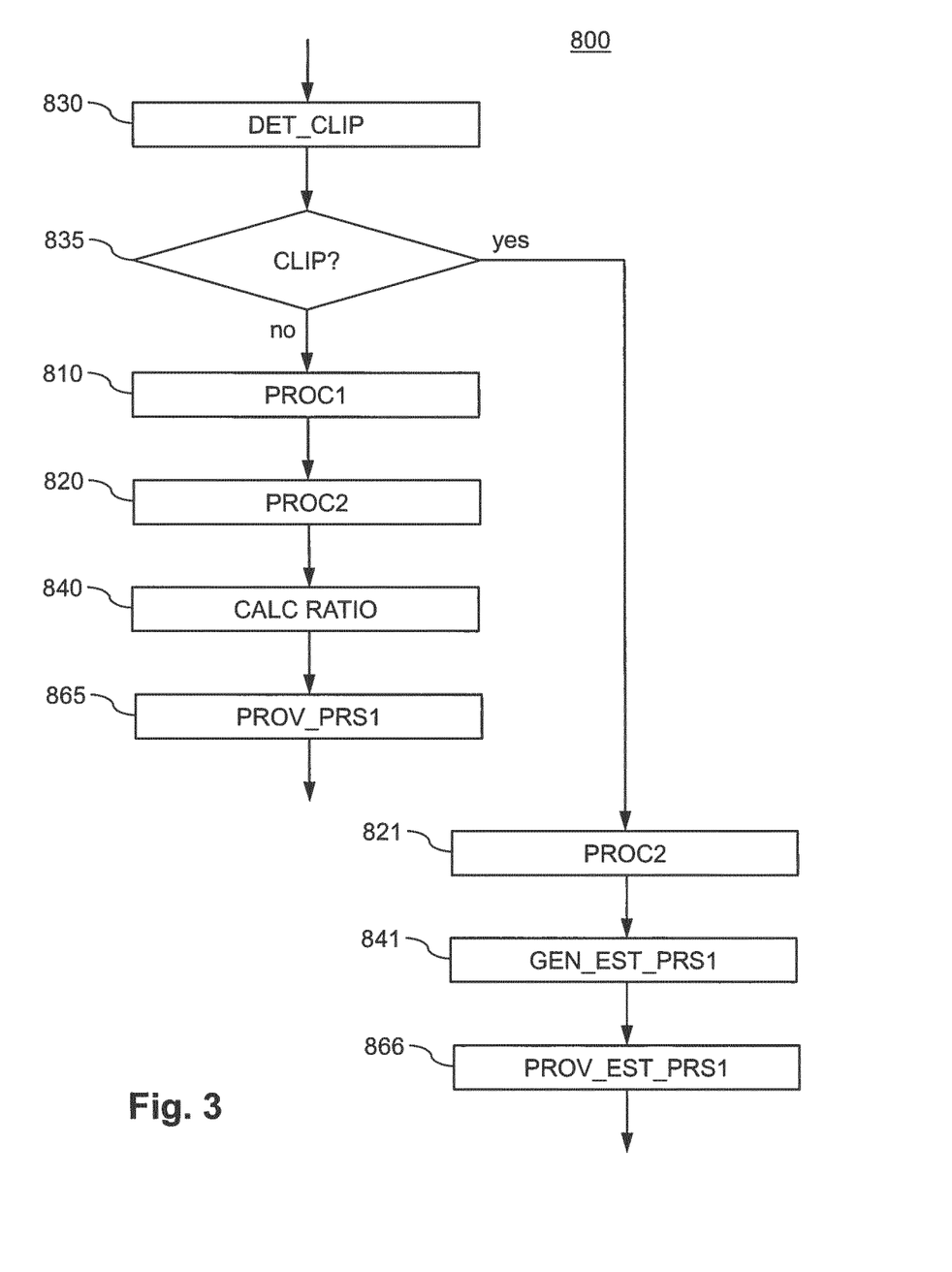
FIG. 3 schematically shows an alternative sleep signal conditioning method for a sleep monitor.

FIG. 3 schematically shows an alternative sleep signal conditioning method 800 for a sleep monitor. The method starts with step DET_CLIP 830 by detecting clipping of a first sensor signal. The method continues by taking a decision CLIP? 835 on what is the next step in the method based on if the first sensor signal is clipping or not.

If the first sensor signal is not clipping the method continues with conditioning PROC1 810 of the first sensor signal and deriving the first parameter indicative of the magnitude thereof. After processing PROC1, the first sensor signal the method continues with conditioning PROC2 820 of the second sensor signal and deriving the second parameter indicative of the magnitude thereof. The processing steps may be swapped in order or executed in parallel. The processing may involve multiple samples of the signal, e.g. a FIR or IIR filtering. Deriving the parameter indicative of the magnitude of the signal may be an energy estimation of the signal. The energy of a signal is typically represented by the quadrate of the signal. Another example of processing may be to take the absolute value of the signal. The processing unit may also comprise a combination of the above processing examples.

The processing of the second sensor signal may be temporarily halted if the second sensor signal is clipping. The processing of the first sensor signal may also be temporarily halted if the first and second sensor signals are clipping.

After processing the first and second sensor signals, the method continuous with the step CALC_RATIO 840 of calculating a ratio. The ratio is based on dividing the first parameter by the second parameter when the first sensor signal is not clipping. Thereto parameter values may be buffered during clipping, the buffered values being used during clipping.

After calculating the ratio, the method continues with the step PROV_PRS1 865 of providing the first conditioned signal to the first output. The step of providing may be done any moment in time after processing PROC1 of the first sensor signal, thus this step may be swapped with or executed in parallel to the steps of processing the second sensor signal or calculating. Next, the method continues with the step of detect clipping DET_CLIP.

If the first sensor signal is clipping at step CLIP? the method continues with step PROC2 821 of conditioning the second sensor signal. The processing of the second sensor signal may depend on detecting if the second sensor signal is also clipping.

After processing the second sensor signal, or directly after the decision that the first sensor signal is clipping, the method continues with the step GEN_EST_PRS1 841 of generating an estimated first sensor signal. The estimated first processed signal is based on the multiplication of the second conditioned signal with the ratio. The processing of the second sensor signal may be halted if it is detected that the second sensor signal is also clipping, while the multiplier may use a previous value of the second conditioned signal in the multiplication. The method continues with the step PROV_EST_PRS1 866 of providing the estimated first sensor signal to the sleep signal output. The method continues with the step of detect clipping 830.

The method or device may also provide further conditioned signals to a further sleep signal outputs.

In an embodiment the method or device may also provide one or more clipping signals to respective clip signal outputs.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Figure 4:
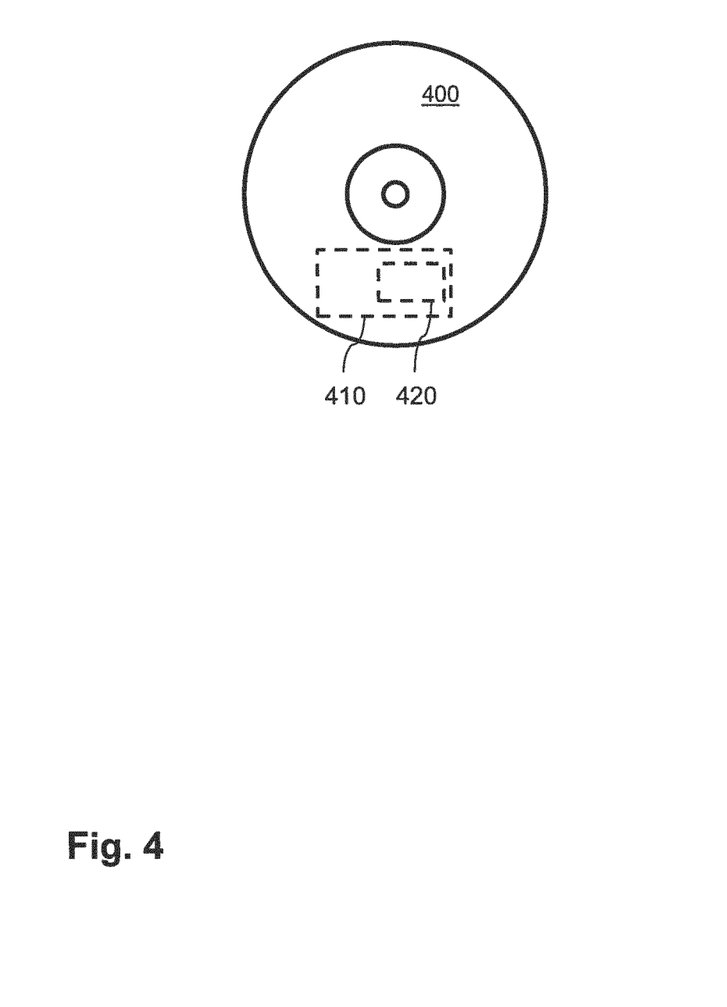
FIG. 4 schematically shows an embodiment of a computer program product, computer readable medium and/or non-transitory computer readable storage medium according to the invention.

FIG. 4 schematically shows an embodiment of a computer program product, computer readable medium and/or non-transitory computer readable storage medium 400 having a writable part 410 including a computer program 420, the computer program including instructions for causing a processor system to perform a method according to the invention.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

Examples, embodiments or optional features, whether indicated as non-limiting or not, are not to be understood as limiting the invention as claimed.

The invention claimed is:

1. A sleep signal conditioning device for a sleep monitor, the device comprising:
   a first processing unit for providing a first parameter indicative of the magnitude of a first sensor signal from a first sleep sensor sensing a physiological signal from a sleeping mammal;
   a second processing unit for providing a second parameter indicative of the magnitude of a second sensor signal from a second sleep sensor sensing a physiological signal from the sleeping mammal, wherein the first sensor signal is different from the second sensor signal;
   a clipping detector for detecting when the first sensor signal is clipping;
   a divider for calculating a ratio based on dividing the first parameter by the second parameter when the first sensor signal is not clipping;
   a multiplier for generating an estimated first sensor signal based on multiplying a second output signal based on the second sensor signal by the ratio; and
   a switch for providing a first output sleep signal based on the estimated first sensor signal when detecting that the first sensor signal is clipping and a first output signal based on the first sensor signal when detecting that the first sensor signal is not clipping.

2. The device according to claim 1, wherein the first and second processing unit are arranged to provide an amplitude or an energy as the parameter indicative of the magnitude of the signal.

3. The device according to claim 1, wherein the first and second processing units comprise an IIR filter and/or FIR filter.

4. The device according to claim 1, wherein at least one of the processing units is arranged to determine the parameter indicative of the magnitude of the signal based also on a signal portion after a preceding signal portion where the first sensor signal was clipping, while the divider is arranged to use the determined parameter in the calculation of the ratio used during said preceding signal portion.

5. The device according to claim 1, wherein an ability to extract respiratory and cardiac features from a current signal portion is determined and the divider is arranged in dependence thereon to control whether or not to include the current signal portion in the calculation of the ratio.

6. The device according to claim 1, wherein the device comprises a first conditioning unit for conditioning the first sensor signal to the first output signal and a second conditioning unit for conditioning the second sensor signal to the second output signal, or
   the first parameter as provided by the first processing circuit constitutes the first output signal and the second parameter as provided by the second processing circuit constitutes the second output signal.

7. The device according to claim 1, wherein the device comprises a second clipping detector for detecting when the second sensor signal is clipping; and the divider is arranged for calculating the ratio when the second sensor signal is not clipping.

8. The device according to claim 1, comprising:
a plurality of processing units for processing a plurality of sensor signals from a respective plurality of sleep sensors;
a plurality of clipping detectors for detecting when a respective one of the sensor signals is clipping;
at least one divider for calculating a ratio matrix, wherein each element of the ratio matrix is a ratio based on dividing, when the respective sensor signals are not clipping, respective parameters indicative of the amplitude of respective sensor signals;
at least one multiplier for generating at least one respective estimated signal based on multiplying a selected output signal based on a selected other one of the sensor signals by the respective element of the ratio matrix; and
a plurality of switches for providing per switch a respective sleep output signal based on the respective estimated signal when detecting that the respective signal is clipping and based on a respective output signal based on the respective signal when detecting that the respective signal is not clipping.

9. A sleep monitoring system comprising:
a first processing unit for providing a first parameter indicative of the magnitude of a first sensor signal from a first sleep sensor sensing a physiological signal from a sleeping mammal;
a second processing unit for providing a second parameter indicative of the magnitude of a second sensor signal from a second sleep sensor sensing a physiological signal from a sleeping mammal, wherein the first sensor signal is different from the second sensor signal;
a clipping detector for detecting when the first sensor signal is clipping;
a divider for calculating a ratio based on dividing the first parameter by the second parameter when the first sensor signal is not clipping;
a multiplier for generating an estimated first sensor signal based on multiplying a second output signal based on the second sensor signal by the ratio; and
a switch for providing a first output sleep signal based on the estimated first sensor signal when detecting that the first sensor signal is clipping and a first output signal based on the first sensor signal when detecting that the first sensor signal is not clipping;
a sleep monitor for monitoring the sleep output signal received from the sleep signal conditioning device.

10. A system according to claim 9 comprising a mattress, wherein the first and second sleep sensor are positioned in, adjacent of or in proximity of the mattress for measuring the mammal asleep on the mattress.

11. A system according to claim 9, wherein the first and second sensors have a different dynamic range and/or accuracy.

12. A system according to claim 9, wherein the first and second sensors are piezoelectric sensors.

13. A system according to claim 9, wherein the first and second sensor are pressure sensors for sensing the physiological signal.

14. A sleep signal conditioning method for a sleep monitor, comprising the steps of:
processing a first sensor signal for providing a first parameter indicative of the magnitude of the first sensor signal from a first sleep sensor sensing a physiological signal from a sleeping mammal;
processing a second sensor signal for providing a second parameter indicative of the magnitude of the second sensor signal from a second sleep sensor sensing a physiological signal from the sleeping mammal, wherein the first sensor signal is different from the second sensor signal;
detecting when the first sensor signal is clipping;
calculating a ratio based on dividing the first parameter by the second parameter when the first sensor signal is not clipping;
generating an estimated first sensor signal based on multiplying a second output signal based on the second sensor signal by the ratio; and
a switch for providing a first output sleep signal based on the estimated first sensor signal when detecting that the first sensor signal is clipping and a first output signal based on the first sensor signal when detecting that the first sensor signal is not clipping; and
providing the first output sleep signal based on the estimated first sensor signal when detecting that the first sensor signal is clipping and the first output signal based on the first sensor signal when detecting that the first sensor signal is not clipping.

15. A computer program product comprising a nontransitory computer readable medium having computer readable code embodied therein, the computer readable code being configured such that, on execution by a suitable computer or processor, the computer or processor is caused to perform the method of claim 14.

* * * * *